(12) United States Patent
Nijs et al.

(10) Patent No.: US 7,972,318 B2
(45) Date of Patent: Jul. 5, 2011

(54) INDIVIDUALLY-PACKAGED HYGIENE ARTICLE AND ABSORBENT ARTICLE PROVIDED THEREWITH

(75) Inventors: Brigitte Louisette Camille Nijs, Kelkheim (DE); Stefan Brouwers, Kellkheim (DE); Harald Giebels, Frankfurt-Höchst (DE); Pilar López, Cerdanyola del Valles (ES); Francisco Playá, Calella (ES); Jose Manuel Colacios Ruiz, Terrassa (DE); Helmut Peter Thomann, Schwalbach am Taunus (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/501,512

(22) Filed: Aug. 9, 2006

(65) Prior Publication Data

US 2007/0038197 A1 Feb. 15, 2007

(51) Int. Cl.
*A61F 13/15* (2006.01)
*A61L 15/00* (2006.01)
(52) U.S. Cl. ............... 604/385.02; 604/385.06; 206/440
(58) Field of Classification Search ............. 604/385.02, 604/385.06; 206/440, 438, 210
See application file for complete search history.

(56) References Cited

U.S. PATENT DOCUMENTS

| | | |
|---|---|---|
| 2,834,459 A | 5/1958 | Bletzinger et al. |
| 3,326,450 A | 6/1967 | Langdon |
| 4,191,609 A | 3/1980 | Trokhan |
| 4,342,314 A | 8/1982 | Radel et al. |
| 4,428,477 A | 1/1984 | Cristofolo |
| 4,463,045 A | 7/1984 | Ahr et al. |
| 4,481,243 A | 11/1984 | Allen |
| 4,556,146 A | 12/1985 | Swanson et al. |
| 4,589,876 A | 5/1986 | Van Tilburg |
| 4,687,478 A | 8/1987 | Van Tillburg |
| 4,701,178 A | 10/1987 | Glaug et al. |
| RE32,649 E | 4/1988 | Brandt et al. |
| 4,738,678 A | 4/1988 | Paulis |
| 4,755,421 A | 7/1988 | Manning et al. |
| 4,759,754 A | 7/1988 | Korpman |
| 4,790,840 A | 12/1988 | Cortina |
| 4,808,175 A | 2/1989 | Hansen |
| 4,848,572 A | 7/1989 | Herrea |
| 5,241,710 A | 9/1993 | Lockhart |
| 5,350,067 A | 9/1994 | Beltran |
| 5,413,568 A | 5/1995 | Roach et al. |
| 5,462,166 A | 10/1995 | Minton et al. |
| 5,484,636 A | 1/1996 | Berg et al. |
| 5,531,325 A | 7/1996 | Deflander |
| 5,569,230 A | 10/1996 | Fisher et al. |
| 5,595,807 A | 1/1997 | Gooding, Jr. et al. |

(Continued)

FOREIGN PATENT DOCUMENTS

FR  1 356 311  3/1964

(Continued)

OTHER PUBLICATIONS

European Search Report dated Jan. 17, 2006.

*Primary Examiner* — Jacqueline F Stephens
(74) *Attorney, Agent, or Firm* — Amanda T. Barry; David M. Weirich

(57) ABSTRACT

A package containing a hygiene article which opens in a way preventing the hygiene article from falling out unintentionally. Further, combined absorbent articles are disclosed, wherein a package comprising a hygiene article is joined to an individually-packaged absorbent article.

13 Claims, 2 Drawing Sheets

U.S. PATENT DOCUMENTS

| | | |
|---|---|---|
| 5,648,083 A | 7/1997 | Blieszner et al. |
| 5,662,758 A | 9/1997 | Hamilton et al. |
| 5,702,379 A | 12/1997 | Preiss |
| 5,800,654 A | 9/1998 | Davis et al. |
| 5,860,744 A | 1/1999 | Schulz |
| 6,074,376 A | 6/2000 | Mills |
| 6,083,854 A | 7/2000 | Bogdanski et al. |
| 6,099,940 A | 8/2000 | Hamilton et al. |
| 6,168,508 B1 | 1/2001 | Nagahara et al. |
| 6,280,529 B1 | 8/2001 | Meyer |
| 6,391,011 B1 | 5/2002 | Davis et al. |
| 6,911,022 B2 | 6/2005 | Steger et al. |
| 6,960,349 B2 | 11/2005 | Shantz et al. |
| 2004/0168947 A1 | 9/2004 | McDonald |
| 2005/0192552 A1 | 9/2005 | Steger et al. |
| 2005/0261655 A1 | 11/2005 | Nijs et al. |
| 2007/0131570 A1 | 6/2007 | Nijs et al. |

FOREIGN PATENT DOCUMENTS

| | | |
|---|---|---|
| FR | 2 778 568 | 11/1999 |
| FR | 2819487 | 7/2002 |
| WO | WO 93/09743 | 5/1993 |
| WO | WO 98/53782 | 12/1998 |

INDIVIDUALLY-PACKAGED HYGIENE ARTICLE AND ABSORBENT ARTICLE PROVIDED THEREWITH

FIELD OF THE INVENTION

The present invention relates to the field of sanitary absorbent articles of personal hygiene. A particular focus of the present invention is absorbent articles of feminine hygiene. The present invention provides a package containing a hygiene article, which opens in a way preventing the hygiene article from falling out unintentionally. Further, combined absorbent articles are disclosed, wherein a package comprising a hygiene article is joined to an individually-packaged absorbent article.

BACKGROUND OF THE INVENTION

Absorbent articles for absorbing and handling body exudates, such as diapers, sanitary napkins, panty liners, bed pads and the like are widely known in the art. Due to the different hygienic needs articles like sanitary napkins are often individually wrapped, whereas diapers, panty liners or bed pads are often packaged as a stack in a common package. It has been recognized that changing such absorbent articles can be a hygienic challenge, as portions of the user's body need to be cleaned, as well as the hands of the person changing the article may become contaminated. This can be embarrassing and can soil the replacement absorbent article or the user's closing or other possessions.

It is widely known in the art to use wipes for cleaning of skin portions, which were soiled with body exudates. For instance the use of moistened baby wipes is widely practiced. Such wipes are generally made of a textile material and are oftentimes provided with a moist lotion, which eases cleaning and delivery skin benefits to the skin portion treated therewith. For maintaining the moistness of the wipe these wipes may be packaged in wrappers with barrier properties. Exemplary packaged moistened wipes are disclosed e.g. in U.S. Pat. No. 4,428,477. Typically, cleaning wipes are packaged in stacks in a common package, such as in case of moist baby wipes. In other instances, such as in case of cleaning wipes supplied in airplanes, there is only one wipe individually packaged in a wrapper.

Currently, when attempting to change a soiled absorbent article, such as a loaded sanitary napkin, the user or the person changing the article has to carry the package containing the article for changing as well as another package containing the wipe for cleaning. This is clearly disadvantageous because opening/handling and disposing of a multiplicity of items and especially packages is required. Solutions to this problem are suggested by e.g. U.S. Pat. Nos. 5,350,067; 4,808,175 or 5,569,230. These documents suggest individual absorbent articles comprising an individually-packaged moistened wipe in or on the package of the absorbent article. In other words, absorbent article and wet wipe are always fixedly combined with each other. These combined absorbent articles are an improvement over prior approaches because the number of parts and also waste parts, which must be handled, is reduced as the packages of the absorbent article and the wipe are connected with each other. However, receptacles for the cleaning wipes disclosed in the prior art are conventional pouches. When such pouches are opened by the user for dispensing the cleaning wipe, such as by breaking seal lines or the like, the pouch is converted into a flat piece of material. Hence, the cleaning wipe is not securely contained anymore directly after the process of opening the pouch and can thus fall on the floor unintentionally.

Therefore, it would be desirable to provide a package for a wipe which is easy to handle and to open and which provides protection for the wipe from falling out of the opened package.

Further, it would be desirable to provide combined absorbent articles being provided with an additional hygiene article, such as a wipe, wherein the combined absorbent article has the advantages of increased convenience by reducing the number of items to be handled during the change of the absorbent article, while offering improved handling and better hygiene.

SUMMARY OF THE INVENTION

The present invention is directed to a package enclosing a hygiene article, the package comprising two segments of package material of substantially equal size and shape being disposed on each other congruently, such that the edges of the segments define the periphery of the package. A hygiene article is sandwiched between the two segments of package material. A rupturable seal is arranged along at least part of the periphery of the package and a permanent seal line joining the segments of package material is disposed along part of the periphery of the package, wherein the permanent seal line is capable of resisting a greater tear force than the rupturable seal, and wherein the permanent seal line and the rupturable seal are arranged such that the hygiene article is completely enclosed. The package also includes a grip portion arranged at the periphery of the package outside the permanent seal line, wherein in the grip portion the two segments of package material are not joined at the periphery of the package, such that free flaps are formed, which are individually graspable for the user, and wherein the grip portion is arranged asymmetrically with respect to the permanent seal line.

DETAILED DESCRIPTION OF THE INVENTION

Figure 1:
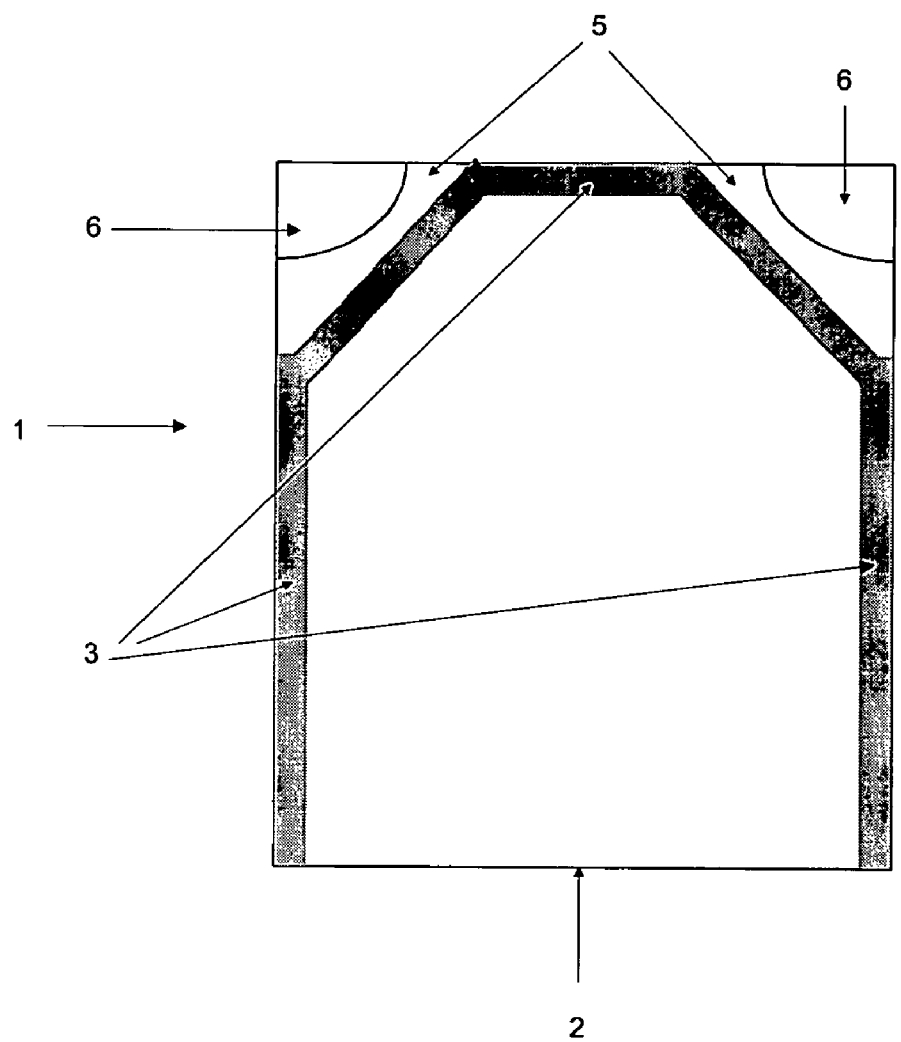
FIG. 1 illustrates an exemplary execution of the package according to the present invention in closed configuration.

The term 'absorbent article' is used herein in a very broad sense including any article being able to receive and/or absorb and/or contain and/or retain fluids and/or exudates, especially bodily fluids/bodily exudates. The absorbent article, which is referred to in the present invention typically comprises a fluid pervious topsheet as the wearer-facing layer, a fluid impervious backsheet as the garment-facing layer that is preferably water vapour and/or gas pervious and an absorbent core comprised there between. Furthermore, absorbent articles in the context of the present invention are typically provided with a means for their attachment to the user's garment, in particular with an adhesive. The absorbent articles of the present invention may be disposable absorbent articles. Typical disposable absorbent articles according to the present invention are absorbent articles for personal hygiene, such as baby care articles like baby diapers; incontinence pads and perspiration pads like underarm sweat pads or hat bands; and articles for feminine hygiene like sanitary napkins and panty liners.

The term 'disposable' is used herein to describe articles, which are not intended to be laundered or otherwise restored or reused as an article (i.e. they are intended to be discarded after a single use and preferably to be recycled, composted or otherwise disposed of in an environmentally compatible manner).

'Individually packaged' as used herein means that only one absorbent article or hygiene article is packaged in an individual package.

A 'permanent seal line' as used herein means a connection between the two segments of package material, which has a higher tear resistance than the rupturable seal. Permanent seal lines suitable herein can be produced by folding a piece of package material such that the fold line bisects the package material piece into two segments of substantially equal size and shape, which can be folded onto each other congruently. Other suitable options for the permanent seal line are heat or pressure sealing lines or lines of adhesive joining both segments of package material to each other along a part of their periphery. The permanent seal line herein is continuous along its length and extends along about 10% to about 50%, about 20%, or about 25% of the periphery of the package. The permanent seal line may be straight, curved, or any shape.

A 'rupturable seal' as used herein refers to a connection between the two segments of package material having a lower tear resistance than the permanent seal line. The rupturable seal can extend along the entire periphery of the package but is generally only present along the portion of the package's periphery where the permanent seal line is not present. Both the permanent seal line and the rupturable seal may be configured such that the hygiene article is completely sealed in the package against the outside environment. Suitable procedures for forming the rupturable seal line are lines heat or pressure bonding or lines of adhesive being arranged along the periphery of the package.

The 'periphery' of the package herein refers to the outer circumference of the package when the package lies flat on a surface.

'Distance' herein means the shortest connection between two points along the periphery of the package.

The 'central line' of the package herein refers to a line originating at half the length of the permanent seal line and extending perpendicularly to the permanent seal line across the package in case of straight permanent seal lines, or radially to the permanent seal line across the package in case of curved permanent seal lines.

The 'point of intercept' herein refers to the intercept of the central line of the package with the periphery of the package opposite the permanent seal line.

Although the package may have a similar shape as the hygiene article packaged therein, the package for the hygiene article according to the present invention can have any shape. Possible shapes include circular, ellipsoidal, semicircular or semi ellipsoidal, triangular, quadrangular, polyangular or irregular shapes. In the event the permanent seal line is a fold line, the shape of the package generally includes at least one straight side edge.

The package is designed to be opened by pulling apart free flaps of the two segments of package material in the grip zone. The grip zone is located on the periphery of the package in an area where the permanent seal line is not present. The 'grip zone' as referred to herein means a zone in the periphery of the package, where the segments of the package material are not sealed to each other, i.e. the rupturable seal is arranged more towards the center of the package in the grip zone. Because they are not sealed to each other, the segments of the package material can be grasped individually in the grip zone. These graspable portions of the package material segments in the grip zone are referred to as 'free flaps'. The grip zone is arranged such that the package opens incompletely for assuming a pouch-like configuration even after being opened. This prevents the hygiene article from falling out unintentionally. Therefore, the grip zone is located asymmetrically with respect to the permanent seal line of the package material. Being arranged 'asymmetrically' with respect to the permanent seal line as used herein means that the grip zone is located outside the central line of the package. 'Central line' of the package herein refers to a line originating at half length of the permanent seal line and extending perpendicularly to the permanent seal line along the package in case of straight permanent seal lines, or radially to the permanent seal line along the package in case of curved permanent seal lines. As an illustrative example, in a quadrangular package, where the permanent seal line is a fold line as described hereinbefore, the grip zone would be arranged in a corner, which is preferably not adjacent the fold line. Other examples can be derived from the figures. The grip zone may be located along the periphery of the package in a distance interval of from about 10% to about 90% of the distance along the periphery of the package starting from one end of the permanent seal line and extending to the intercept point of the central line with the periphery of the package opposite the permanent seal line. The grip zone may be located in the interval from about 50% to about 90%, from about 50% to about 70% of the distance along the periphery of the package starting from one end of the permanent seal line and extending to the intercept point of the central line with the periphery of the package opposite the permanent seal line. The grip zone herein typically has a length of from about 50 to about 300 mm, but can be made larger or smaller as desired. The package of the present invention can have more than one grip zone along its periphery. In one embodiment, as illustrated in FIGS. 1 and 2 herein, the package is provided with two grip zones.

The package of the hygiene article herein may have barrier properties for preventing evaporation of moisture from the hygiene article. Suitable package materials herein are flexible film materials. These flexible film materials can be with or without extra barrier properties towards moisture and oxygen. Suitable barrier materials are laminates, where a layer of EVOH (ethylene vinyl alcohol) or PVOH (propylene vinyl alcohol) or aluminium is sandwiched between polymeric film layers, such as LDPE (low density polyethylene), PP (polypropylene), PET (polyethylene terephtalate) or the like. Further suitable barrier materials for forming the package for the cleaning wipe herein are metallised, particularly aluminised plastic films; metal foils; oriented polyethylene terephtalate (PET); PETG (glycol-modified PET); oriented polyamide; aromatic polyamide; or polymeric films like polyethylene films with special lacquer coatings, which provide the polymeric film with the vapour barrier functionality. Basically every material known in the art for this purpose is suitable for use herein. Additionally flexible film materials with peelable inner layer polymer film or film coated with peelable properties are most suited to provide the extra convenience of ease of opening of the package. One exemplary laminate material particularly suitable as package material herein is disclosed in EP 696,991. This material is a laminate with a PE (polyethylene) bottom layer, on top of which a layer of aluminium foil or optionally aluminized PE is attached with an adhesive. On top of the aluminium or aluminized layer a co-extruded layer of OPP (oriented polypropylene) and PE is attached with an adhesive, with the OPP side facing the aluminium or aluminized layer and the PE side facing outward. Peelable PE films offered by a large range of polymeric film producers can be used as inner layer for subject sachet flexible film composition.

The hygiene article herein may be a wipe, and may be moistened. Moistening is conventionally facilitated by applying a lotion to the wipe substrate. Suitable lotions are aqueous or non-aqueous ones, having fluid-like viscoelastic properties at room temperature. Lotions for use herein may increase the cleaning capabilities of the wipe by aiding removal of soiling from the skin. Further, lotions for use herein may also provide skin benefits by reducing friction between the skin and the wipe and/or by containing materials like Aloe vera or chamomile, which increase skin health. Lotions are provided to the cleaning wipe in an amount such that the wipe is noticeably moist to the user and that the functional capacities of the functional wipe, such as cleaning, are increased. Applying lotion to the wipe in an amount such that the lotion drips off from the wipe without exertion of pressure, such as by wringing out, is less desirable herein. Examples for suitable lotions are disclosed in EP-A-808,151; EP-A-763,341 or WO 00/57843.

Figure 2:
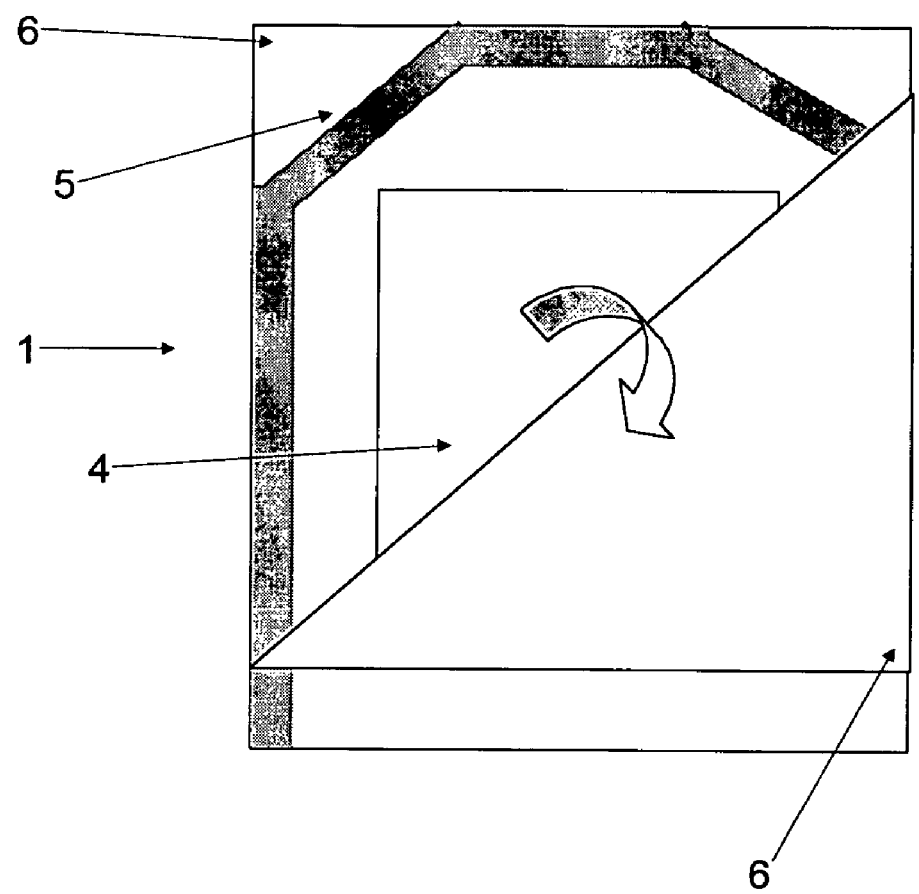
FIG. 2 illustrates the execution illustrated in FIG. 1 is partially opened configuration.

An exemplary execution of the package of the present invention is illustrated in FIGS. 1 and 2. Such a package 1 is formed by folding a rectangular piece of flexible package material onto itself, such that the fold line 2 bisects the package material into two segments of equal size and shape, which are disposed on each other congruently. The fold line 2 forms in this embodiment the permanent seal line. The remaining open side edges of the thus-formed rectangular package 1 are sealed by breakable heat seals 3. Both the fold line 2 and the breakable heat seals 3 encircle a folded lotioned wipe 4, which has been sandwiched between the two segments of package material. On the two corners of the package 1, which are not adjacent the fold line 2, the breakable heat seal 3 is spaced away from the periphery of the package 1. By this grip portions 5 are generated. Consequently, the breakable heat seal assumes a configuration, which can be described as arcuate. In each grip portion 5 the two segments of package material are not sealed to each other. Thus, each of the two segments can be grasped individually by the user. These individually graspable portions of the package material in the grip portion 5 are referred to as free flaps 6. The free flaps 6 can be provided with a grasping aid in the form of a cutout as illustrated in FIG. 1.

FIG. 2 illustrates the process of opening of the package 1. For facilitating this in a grip portion 5 both free flaps 6 are pulled apart from each other. By this, the breakable heat seal 3 breaks asymmetrically with respect to the fold line 2 so that the opened package 1 assumes a pouch-like configuration.

The present invention also provides a combined absorbent article, where an individually-packaged hygiene article, which packed in the package of the first aspect of the present invention is joined to an individually-packaged absorbent article. Thereby, a combined absorbent article is created. 'Combined absorbent article' as used herein means an individually-packaged absorbent article with a packaged hygiene article, preferably an individually one, joined thereto. Typically the hygiene article is a wipe. The manner of joining can be either fixedly or releasably. Most conveniently, for ease of handling, the package containing the hygiene article is joined to the exposed surface of the package of the individually-packaged absorbent article.

Although the preceding description exclusively refers to individually packaged absorbent articles and hygiene articles it is also encompassed by the present invention that any number of absorbent articles or hygiene articles can be packaged together in one package.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package enclosing a wipe, the package comprising:
   two segments of package material of substantially equal size and shape being disposed on each other congruently, such that the edges of the segments define the periphery of the package, the package material providing a moisture barrier;
   a moistened wipe being sandwiched between the two segments of package material;
   a rupturable seal being arranged along at least part of the periphery of the package;
   a permanent seal line joining the segments of package material along from about 25% to about 50% of the periphery of the package, wherein the permanent seal line is capable of resisting a greater tear force than the rupturable seal, and wherein the permanent seal line and the rupturable seal are arranged such that the wipe is completely enclosed;
   a grip portion being arranged at the periphery of the package outside the permanent seal line, wherein in the grip portion the two segments of package material are not joined at the periphery of the package, such that free flaps are formed, which are individually graspable for the user; and wherein the grip portion is arranged asymmetrically with respect to the permanent seal line;
   wherein the package is joined to an individually-packaged absorbent article, and wherein the package forms a pouch-like configuration when opened.

2. The package of claim 1, wherein the rupturable seal is present along the periphery of the package where the permanent seal line is not present.

3. The package of claim 1, wherein the grip portion has a length of from about 50 mm to about 300 mm along the periphery of the package.

4. The package of claim 1, wherein the grip portion is located along the periphery of the package in an interval of from about 10% to about 90% of the distance between an end of the permanent seal line and the point of intercept of the central line of the package with the periphery of the package.

5. The package of claim 4, wherein the grip portion is located along the periphery of the package in an interval of from about 50% to about 70% of the distance between an end of the permanent seal line and the point of intercept of the central line of the package with the periphery of the package.

6. The package of claim 1, wherein the package is provided with an opening aid in the grip portion.

7. The package of claim 6, wherein the opening aid includes a cutout in one of the free flaps.

8. The package of claim 1, wherein the package comprises more than one grip portion.

9. The package of claim 8, wherein the package comprises two grip portions.

10. The package of claim 1, wherein the package contains up to ten hygiene articles.

11. The package of claim 1, wherein the package contains up to five hygiene articles.

12. The package of claim 1, wherein the package contains one hygiene article.

13. The package of claim 1, wherein the absorbent article is a sanitary napkin, a panty liner, a tampon, an incontinence article or a perspiration pad.

* * * * *